(12) United States Patent
Braun

(10) Patent No.: US 12,185,963 B2
(45) Date of Patent: Jan. 7, 2025

(54) ELECTRODE APPLICATION INSTRUMENT

(71) Applicant: Tuebingen Scientific Medical GmbH, Tübingen (DE)

(72) Inventor: Marcus Braun, Weil im Schönbuch (DE)

(73) Assignee: Tuebingen Scientific Medical GmbH (DE)

( * ) Notice: Subject to any disclaimer, the term of this patent is extended or adjusted under 35 U.S.C. 154(b) by 1106 days.

(21) Appl. No.: 17/042,563

(22) PCT Filed: Mar. 28, 2019

(86) PCT No.: PCT/EP2019/057946
§ 371 (c)(1),
(2) Date: Sep. 28, 2020

(87) PCT Pub. No.: WO2019/185845
PCT Pub. Date: Oct. 3, 2019

(65) Prior Publication Data
US 2021/0030433 A1 Feb. 4, 2021

(30) Foreign Application Priority Data
Mar. 28, 2018 (DE) .......................... 202018101753.5

(51) Int. Cl.
*A61B 17/29* (2006.01)
*A61N 1/05* (2006.01)
*A61B 17/00* (2006.01)

(52) U.S. Cl.
CPC .......... *A61B 17/2909* (2013.01); *A61N 1/057* (2013.01); *A61B 2017/00243* (2013.01);
(Continued)

(58) Field of Classification Search
CPC ................ A61B 17/29; A61B 17/2909; A61B 2017/2916; A61B 2017/2926;
(Continued)

(56) References Cited

U.S. PATENT DOCUMENTS 5,036,854 A  8/1991 Schollmeyer et al.
5,354,312 A * 10/1994 Brinkerhoff ........... A61B 17/29
                                                          606/205

(Continued)

FOREIGN PATENT DOCUMENTS

CN       101686850 A     3/2010
CN       106456248 A     2/2017
(Continued)

OTHER PUBLICATIONS

Japanese Notice of Reasons of Refusal for Japanese Application No. 2020-552246, with English translation, dated Mar. 3, 2023, 12 pages.

(Continued)

*Primary Examiner* — Darwin P Erezo
*Assistant Examiner* — Christian D Knauss
(74) *Attorney, Agent, or Firm* — Buchanan Ingersoll & Rooney PC

(57) ABSTRACT

A surgical electrode application instrument of the minimally invasive type, having an effector which forms a rotatable and pivotable instrument head on which are mounted two opposing branches which can be moved towards each other in the manner of tongs, at least one branch of which is formed with a part-circle-shaped notch at the end for holding an electrode wire, and which each have a sickle-shaped cross-section at least in one section. The mutually facing clamping sides in the sickle-shaped section of each branch each have a number of grooves or undercuts which are spaced in the longitudinal (Continued)

direction of the branch and preferably run in parallel in the transverse direction of the branch.

9 Claims, 4 Drawing Sheets

(52) U.S. Cl.
CPC .............. *A61B 2017/2916* (2013.01); *A61B 2017/2929* (2013.01); *A61B 2017/2936* (2013.01); *A61N 2001/058* (2013.01)

(58) Field of Classification Search
CPC .... A61B 2017/2927; A61B 2017/2929; A61B 2017/2936; A61N 1/05; A61N 2001/0578; A61N 2001/058
See application file for complete search history.

(56) References Cited

U.S. PATENT DOCUMENTS

| | | | |
|---|---|---|---|
| 5,573,535 A | 11/1996 | Viklund | |
| 5,746,740 A | 5/1998 | Nicholas | |
| 5,752,973 A | 5/1998 | Kieturakis | |
| 5,776,150 A * | 7/1998 | Nolan | A61B 17/0469 606/147 |
| 7,544,197 B2 | 6/2009 | Kelsch et al. | |
| 2004/0260334 A1* | 12/2004 | Braun | A61B 17/29 606/208 |
| 2008/0167680 A1 | 7/2008 | Voegele et al. | |
| 2009/0192521 A1 | 7/2009 | Braun | |
| 2010/0305581 A1* | 12/2010 | Hart | A61B 17/0625 606/139 |
| 2011/0160743 A1 | 6/2011 | Espinal | |
| 2016/0022356 A1 | 1/2016 | Schostek et al. | |
| 2016/0279423 A1 | 9/2016 | Kelly et al. | |
| 2017/0135751 A1 | 5/2017 | Rothweiler et al. | |

FOREIGN PATENT DOCUMENTS

| | | | |
|---|---|---|---|
| DE | 4421822 C1 | 10/1995 | |
| DE | 10125149 A1 | 12/2002 | |
| DE | 202004002011 U1 | 4/2004 | |
| DE | 10330604 A1 | 10/2004 | |
| DE | 10324884 A1 | 12/2004 | |
| DE | 102009001278 A1 | 9/2010 | |
| DE | 102013105240 A1 | 11/2014 | |
| EP | 1886630 A2 | 2/2008 | |
| EP | 2377477 A1 | 10/2011 | |
| JP | 0838495 A | 2/1996 | |
| WO | 2004098701 A1 | 11/2004 | |

OTHER PUBLICATIONS

German Search Report for German Application No. 20 2018 101 753.5, with partial English translation, dated Jan. 24, 2019, 9 pages.
International Search Report and Written Opinion for International Application PCT/EP2019/057946, dated Jun. 5, 2019, 7 pages.
English Translation of Office Action for Chinese App. No. 201980023382.0, dated Dec. 26, 2023.
Office Action (The Second Office Action) issued Jul. 16, 2024, by the State Intellectual Property Office, P. R. China in corresponding Chinese Patent Application No. 201980023382.0 and an English translation of the Office Action. (17 pages).

\* cited by examiner

ELECTRODE APPLICATION INSTRUMENT

This application is a United States National Phase entry of International Application No. PCT/EP2019/057946, filed Mar. 28, 2019, which claims the benefit of German Application No. 20 2018 101 753.5, filed Mar. 28, 2018. The contents of International Application No. PCT/EP2019/057946 and German Application No. 20 2018 101 753.5 are incorporated by reference herein in their entireties.

FIELD OF THE INVENTION

The present invention relates to an electrode application instrument of the minimally invasive type according to the preamble of claim 1.

BACKGROUND OF THE INVENTION

In the case of cardiac arrhythmia, for example, pacemakers are often implanted in the patient, which are electrically connected to certain areas of the heart via electrical lines and electrodes mounted at the end of the lines. It is crucial that the electrodes are correctly and safely installed/attached/anchored to the heart. For this purpose, the electrodes have screw-like or corkscrew-like extensions/anchors that are screwed into the muscle tissue of the heart.

Two procedures have been established in the past for the implantation of such electrodes. On the one hand, electrodes of this type can be inserted into the heart via the carotid artery using a catheter and are then fixed in place. This has the advantage that the patient is only slightly injured during the operation (minimal surgical trauma) and the risk of infection can therefore be minimized as far as possible. However, this procedure has the disadvantage that the positioning of the electrodes is difficult and sometimes also inaccurate. On the other hand, electrodes of this type can be placed on the outside of the heart in a minimally invasive manner using a surgical instrument of the shaft type. For this purpose, for example, a minimally invasive patient access is created through which the instrument shaft of the surgical instrument can be inserted.

PRIOR ART

From the prior art according to U.S. Pat. No. 7,544,197B2 for example, an electrode application instrument of the shaft type is known. This instrument has a handhold connected to a proximal end of an instrument shaft, at the distal end of which an effector is pivotably and rotatably mounted. The effector forms a jaw part/instrument head for holding an electrode for its application to the outer wall of a heart. The jaw part is designed in the form of a tulip with three or four circumferentially spaced, spring-elastic tabs that form a kind of holding ring in which an electrode can be clamped. In addition, semicircular recesses or notches are formed between the tabs at the ends, through which the electrode litz wires can be passed when the electrode is clamped in the holding ring.

It has been shown that although a jaw part designed in this way can hold the electrode securely and screw it in, it cannot simply release the electrode after it has been attached to the heart muscle.

SUMMARY OF THE INVENTION

In view of this problem, it is an object of the present invention to provide an electrode application instrument with which the application of electrodes in particular to the heart muscle can be carried out in a simple and safe manner.

This object is solved by a surgical instrument, in particular an electrode application instrument of the minimally invasive type with the features of claim 1. Advantageous further developments of the invention are the subject matter of the dependent claims.

The core of the present invention accordingly consists in the special configuration of the effector or jaw part with two opposite branches which can be moved towards each other in a forceps-like manner, of which at least one branch (preferably both) is formed with a pitch-circular notch (for receiving an electrode litz wire) at the end face and which are each bent or curved in a sickle shape in cross-section (when viewed proximally), whereby a trough shape extending in the longitudinal direction (proximal direction) is formed on the inner sides of the branches facing each other (at least in the area of an engagement portion of the branch). The inner/clamping sides of each branch facing each other also have a number of (inner circumferential) grooves or undercuts spaced apart in the axial direction, which preferably have the same radii or groove depths and serve to (axially) receive an electrode (i.e. to receive the usually button-shaped or plate-shaped electrode not from the side but from above).

It should be noted that already one single groove is sufficient to hold the electrode correctly, i.e. in such a way that the corkscrew-like extension of a generally known electrode is oriented axially to the instrument head/jaw part, wherein a plurality of grooves is advantageous in that a higher torque can be transmitted to the electrode.

The branches of the jaw part are articulated/pivotably mounted on an instrument head and coupled to a handle via an actuating device/gear train. The instrument head is held pivotably and rotatably (about its longitudinal axis) on a distal end of an instrument shaft. The handle is arranged at a proximal end of the instrument shaft, wherein the actuating device/gear train is (at least partially) provided inside the instrument shaft. The handle has a number of actuating elements integrated into a handhold to separately rotate the instrument head about its longitudinal axis, to angle/pivot it with respect to the instrument shaft, and to open/close the branches. Such a basic concept of a surgical instrument of minimally invasive type, in particular the construction of the handle and the design of the instrument head/jaw part, is known, for example, from the printed publications DE 103 24 844 A1, DE 103 30 604 A1 and DE 10 2009 001 278 A1 of the present applicant, so that reference can be made to these publications at this point.

The two branches of the jaw part are preferably identical to each other and further preferably have an axially-offset branch neck in top view or bottom view (direction of view on the clamping side of the engagement portion), which merges distally into an axially centrally arranged engagement portion/gripping portion in one piece. The engagement portion has the sickle-shaped contour in cross-section as described above, preferably has a smooth surface on its radial outside, and has the axially spaced grooves described above which circumferentially extend on its radial inside.

The branch neck is preferably platelet-shaped with a through bore at the distal overlapping portion between the branch neck and a gripping portion and, more preferably, an axially extending elongated hole in the proximal end section of the branch neck, but set at an angle to the longitudinal direction. The platelet-shaped branch neck is preferably rotated by about 90° with respect to the gripping portion in such a way that the through bore and the elongated hole are oriented in the transverse direction of the branch (along the inner circumferential grooves). In this way, the branches in an instrument head can be mounted on the respective through hole in a scissor-like pivoting manner, wherein the respective elongated hole forms a kind of sliding gate, in such a way that, for example, a transverse pin sliding in the instrument head in the longitudinal direction passes through the elongated hole and, during its longitudinal movement, the branch rotates around the hinge as a result of the inclined position of the elongated hole. It should be noted that the translation of the sliding movement of the branch gear train can also be transformed into a pivoting movement of the branches by another mechanism (e.g. via connecting rods).

BRIEF DESCRIPTION OF THE FIGURES

The invention is further explained below by means of a preferred embodiment with reference to the accompanying figures.

DESCRIPTION OF EXEMPLARY EMBODIMENTS

Figure 1:
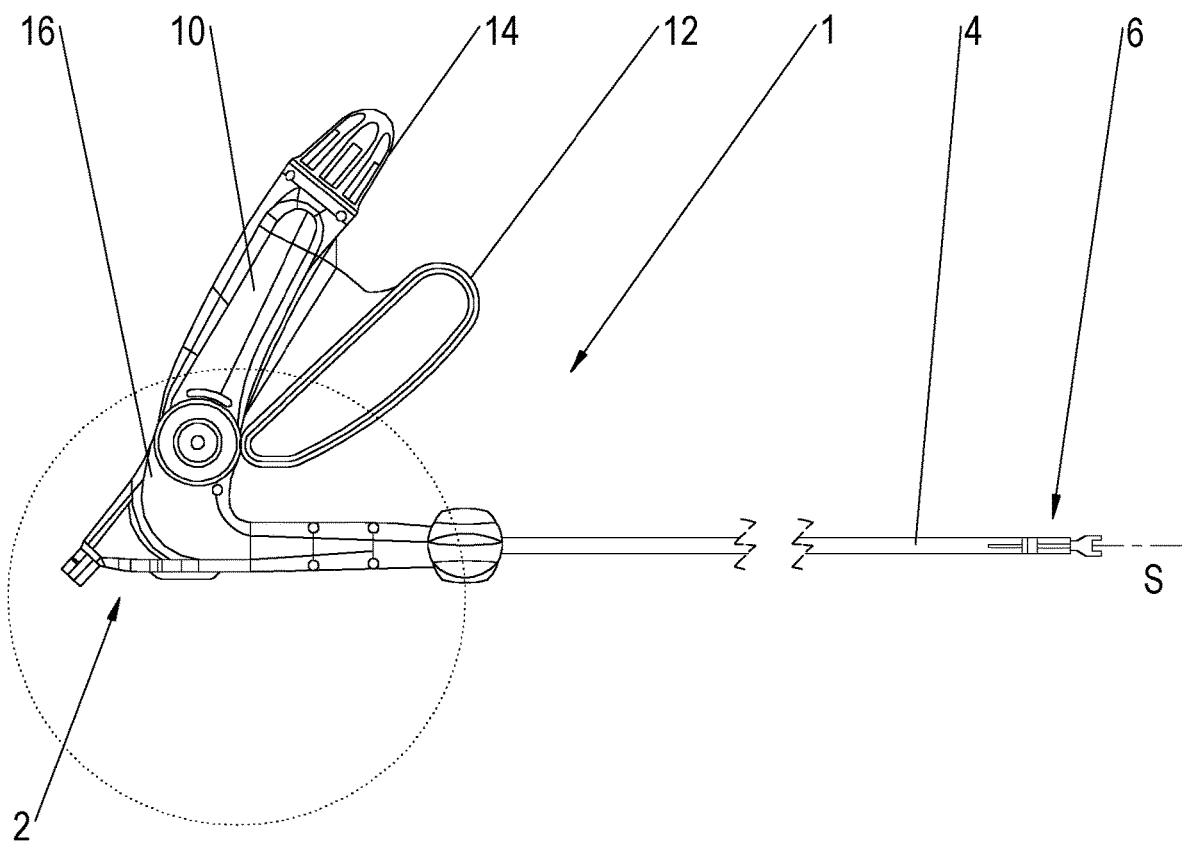
FIG. 1 shows a surgical electrode application instrument according to a preferred embodiment of the present invention.

The surgical instrument 1 shown in FIG. 1 for the application of electrodes (not shown in further detail), for example on a patient's heart, has a handle 2 in the form of a handle piece mounted on the proximal end of an instrument shaft 4. An effector in the form of an instrument head 6 is mounted on the distal end of the instrument shaft 4, which is mounted on the instrument shaft so that it can rotate about its longitudinal axis S and can be pivoted with respect to the longitudinal axis of the instrument shaft. Two branches 8a, 8b are mounted in/on the instrument head 6 in a scissor-like or forceps-like manner (see in particular FIG. 2), so that they can be rotated and pivoted together with the instrument head 6 and can be opened and closed independently of this.

A number of actuating elements (preferably three actuating elements) 10, 12, 14 are arranged on the handle piece/instrument handle 2. As a first point, the instrument handle 2 has a type of control stick 10, which is mounted on a handle base 16 so that it can be pivoted or folded down and is coupled to the instrument head 6 via a gear train guided in the instrument shaft 4 in such a way that a pivoting movement of the control stick 10 with respect to the handle base 16 is transformed into a pivoting movement of the instrument head 6 with respect to the instrument shaft 4. In addition, a pivot lever 12 is hinged to the control stick 10, the pivoting movement of which with respect to the control stick 10 is transmitted to the branches 8 a, 8 b via a separate gear train 100, also guided in the instrument shaft 4, in order to open and close them like scissors or forceps. Finally, a rotary knob 14 is mounted on the free end of the control stick 10, whose rotation acts on the instrument head 6 via a gear train, also located separately in the instrument shaft 4, in order to rotate the instrument head 6 about its longitudinal axis.

The construction of the handle 2, of the respective separate gear trains, and of the instrument head 6 are known from the prior art in accordance with the above-mentioned documents of the present applicant, so that reference can be made to these documents at this point.

According to the present embodiment of the invention, however, the surgical instrument for the application of electrodes differs from the previously known surgical instruments of the minimally invasive type essentially by the construction of the branches 8a, 8b used according to the invention.

Electrodes of the known type for mounting, for example, on the heart of a patient usually have a coin-shaped or button-shaped (flat and round) electrode head, on the flat underside of which a corkscrew-like screw spiral/anchor is arranged, which can be connected via an electrical litz wire (cable) to a pacemaker, for example. Such an electrode has to be threaded into the heart muscle in order to attach it, wherein it is crucial for its secure hold in the comparatively spongy heart muscle tissue that the screw-in process is carried out as axially along the screw spiral as possible without any rocking or tumbling motion. This means that the electrode has to be grasped and held in such a way that the screw spiral extends essentially axially to the longitudinal axis of the instrument head 6.

In order to achieve this effect, the branches 8a, 8b provided in the instrument 1 according to the invention have a construction as shown in particular in FIGS. 2 to 5.

First of all, it should be noted that the branches 8a, 8b, which are mounted on the instrument head 6 in a scissor-like or forceps-like manner, are preferably identical in construction, so that only one of the two branches has to be described in the following.

Each branch 8a, 8b therefore has a proximal branch neck 80 and a distal gripping portion 82, which is connected to it in one piece (via an intermediate overlapping portion). The gripping portion 82 is formed by a sickle-shaped or trough-shaped plate (see FIG. 5a) as seen in cross-section (in the longitudinal direction of the branch), which has a pitch-circular/semi-circular notch 84 (see FIG. 5b) on its distal end face, which is arranged essentially centrally with respect to the longitudinal branch axis B. A (radial) outer side of the gripping portion 82 preferably has a smooth surface, whereas a (radial) inner side of the gripping portion (hereinafter referred to as clamping side) has a groove profile.

In the preferred embodiment, the groove profile consists of a number of grooves 86 spaced in the branch axis direction, which extend in the transverse direction or in the circumferential direction of the gripping portion 82 and thus essentially perpendicular to the longitudinal branch axis B over the entire gripping portion 82. Furthermore, all grooves 86 preferably have the same radius or groove depth. The groove width also preferably remains the same, but can change starting from distal to proximal.

The branch neck 80 has a plate-like or platelet-like shape and is rotated by essentially 90° around the longitudinal branch axis in relation to the gripping portion 82. This means that while the gripping portion 82 is oriented virtually horizontally, for example, the plate-shaped branch neck 80 extends essentially vertically. At a distal overlapping portion 88 between branch neck 80 and gripping portion 82, a through bore 90 is formed, which, due to the 90° rotation, extends essentially (tangentially) along the grooves 86. An elongated hole 92 is furthermore formed at a proximal end portion of the branch neck 82, which extends along the longitudinal branch axis but which is additionally set at an acute angle (e.g. 15°-20°) to the longitudinal branch axis.

Figure 2:
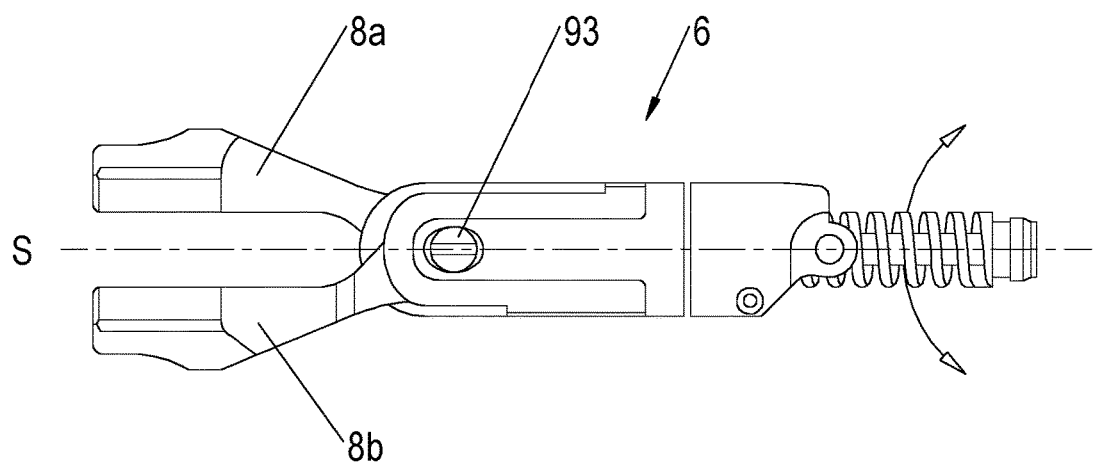
FIG. 2 shows the instrument head of the surgical instrument as shown in FIG. 1.
Figure 3:
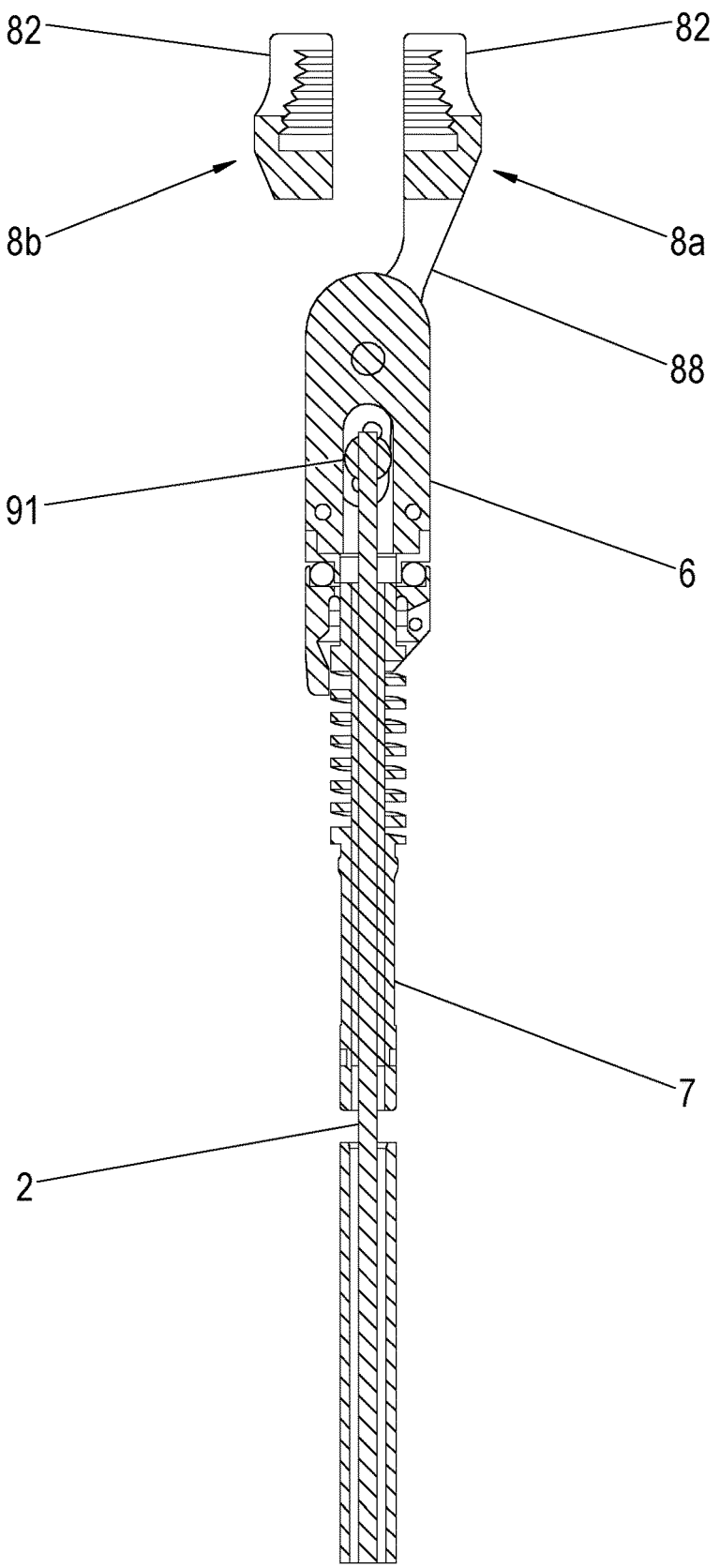
FIG. 3 shows a longitudinal section of the instrument head according to FIG. 2.
Figure 4:
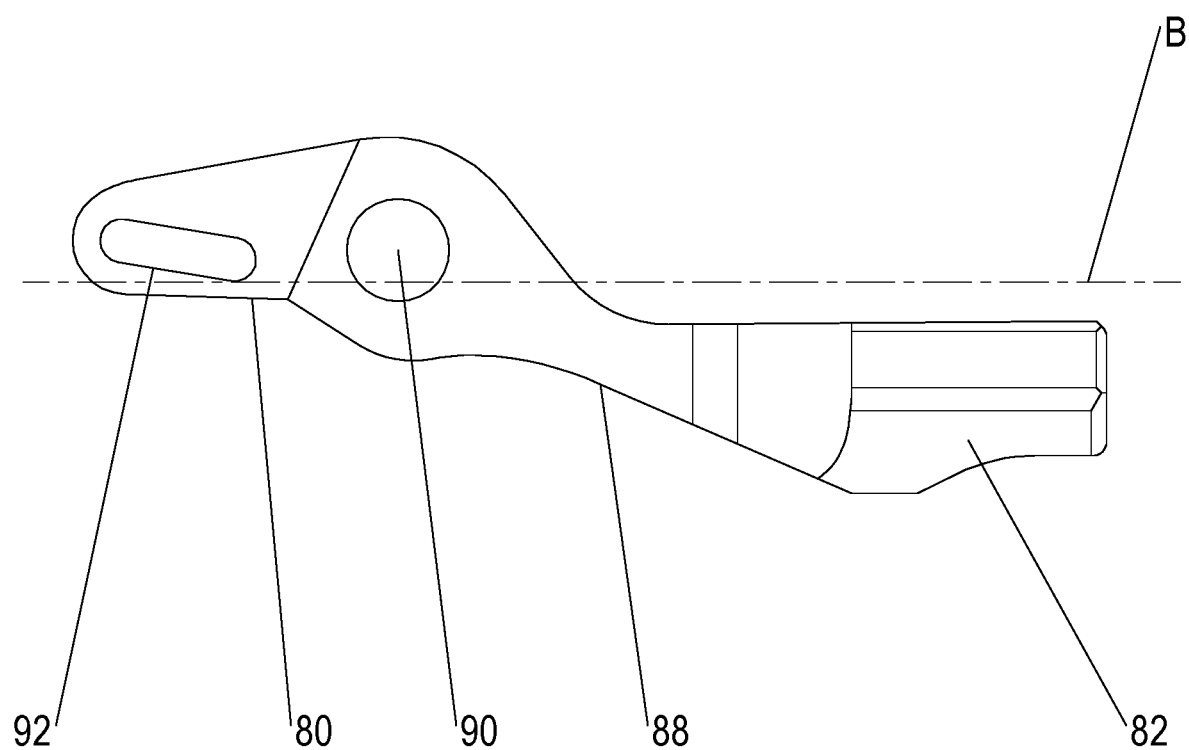
FIG. 4 shows the side view of an instrument branch according to a preferred embodiment of the invention as used on the instrument head according to FIG. 3, FIGS. 5a to 5d show the engagement portion of an instrument branch according to the present invention in cross-section, bottom view and longitudinal section.

As shown in particular in FIG. 4, the longitudinal branch axis in the area of the branch neck 80 and the longitudinal branch axis in the area of the gripping portion 82 run essentially parallel to each other, whereas the longitudinal branch axis B in the overlapping portion 88 between branch neck 80 and gripping portion 82 is set at an angle to it in side view, resulting in an S-shaped branch line in side view. As a result, the two branches 8a, 8b, which are mounted on the instrument head 6 in a scissor-like or forceps-like manner, form a clamping gap between the opposite clamping sides when the two branches 8a, 8b are in a position in which the clamping sides are oriented parallel to each other. This position is shown in FIG. 2, for example.

Figure 5C:
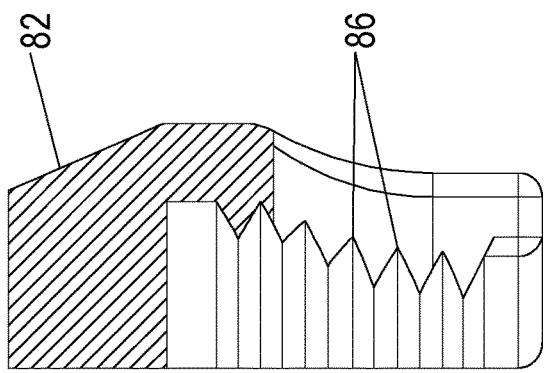
Figure 5B:
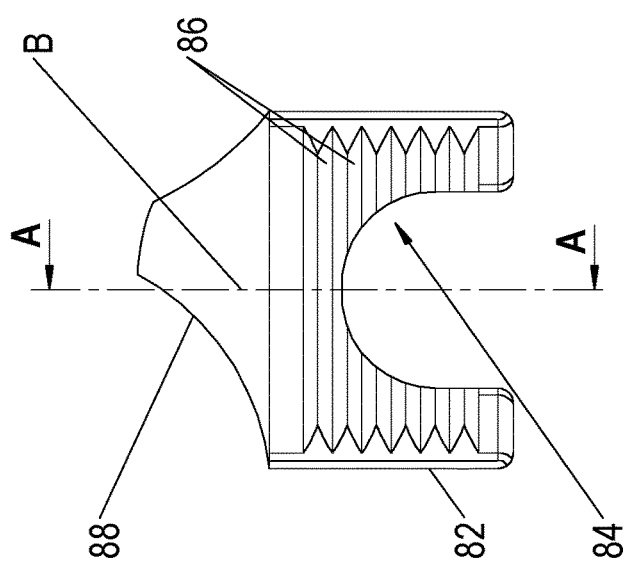
Figure 5A:
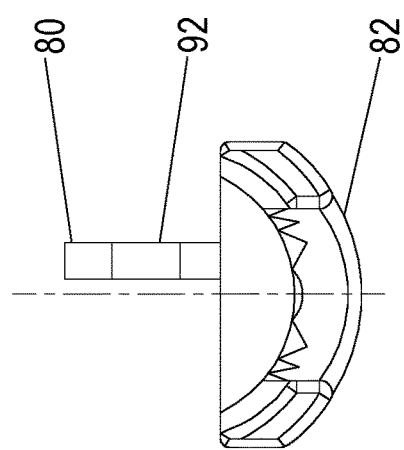
Figure 5D:
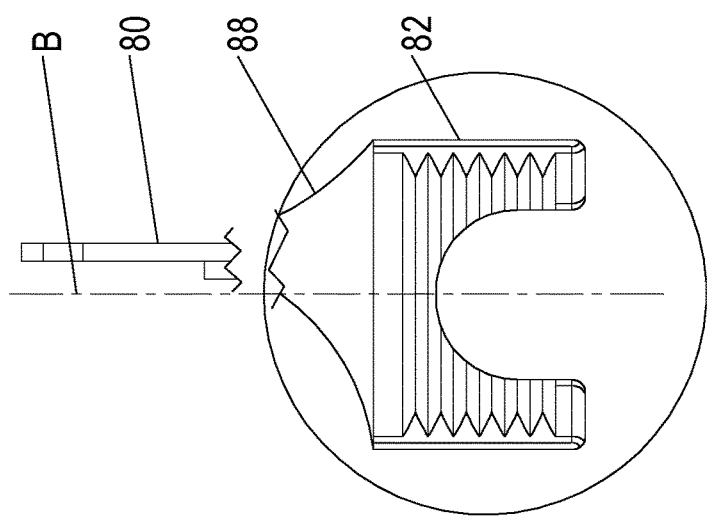

As can be clearly seen in FIGS. 5b and 5d, the branch neck 80 and gripping portion 82 are asymmetrically arranged in the bottom view (i.e. with a view of the clamping side of the gripping portion 82). In other words, the branch neck 80 is offset parallel to the central or longitudinal axis (longitudinal branch axis B) of the gripping portion 82 in such a way that when two branches 8a, 8b lie against each other in the area of the branch neck 82, the two opposite clamping sides are essentially aligned or overlap.

EXEMPLARY FUNCTIONAL PRINCIPLE

For applying an electrode to the outside of a patient's heart, for example, the electrode is grasped at the edge with the branches 8a, 8b mounted on the instrument head in a scissor-like manner so that the edge of the electrode engages in the same grooves on the opposite branches. This ensures that the electrode is oriented essentially perpendicular to the instrument head axis. It is important to ensure that the edge of the electrode is gripped in the groove with a certain radius so that the two branches orient themselves essentially parallel to each other when the electrode is gripped.

The gripping process is essentially performed by actuating the lever 12, whereby a spike or pin 91, which is axially displaceable in the instrument head 6, is longitudinally shifted via the associated gear train in the instrument shaft 4, the spike or pin 91 in turn engaging in the elongated holes 92. Due to the inclined position of the elongated holes 92 in relation to the longitudinal branch axis B or the instrument-head longitudinal axis S, the elongated holes 92 act as guiding slides in such a way that when the spike/pin 91 is moved axially along the elongated holes 92, the branches 8a, 8b are simultaneously rotated about a pivot spike 93 inserted into the through bores 90.

The electrode can now be threaded into the heart muscle by pivoting the instrument head 6 so that it is oriented essentially perpendicular to the outside of the heart and then rotating the instrument head and the branches 8a, 8b forming the jaw part. As soon as the electrode is firmly screwed into the heart muscle, the branches 8a, 8b can be opened and thus the electrode is released.

The invention claimed is:
1. A surgical electrode application instrument of the minimally invasive type, the instrument comprising:
an instrument shaft comprising a distal end and a proximal end;
an effector being arranged at the distal end of the instrument shaft and forming an instrument head being mounted in a rotatable and pivotable manner;
the effector comprising two opposite branches which are pivotably mounted and which can be moved towards each other and away from each other in a scissors-like or forceps-like manner;
wherein at least one branch of the two branches comprises a distal end face and a pitch-circular notch for holding an electrode litz wire;
wherein the notch opens to the distal end face;
wherein the two branches each have a sickle-shaped engagement portion comprising a radial outside and a radial inside;
wherein the radial insides of the sickle-shaped engagement portions of the two branches form mutually facing clamping sides;
wherein the mutually facing clamping sides each have a number of grooves or undercuts which are spaced apart in a longitudinal direction of the branch; and
at least one actuating element being arranged at the proximal end of the instrument shaft and for applying an actuating force;
a downstream gear or power transmission gear being arranged within the instrument shaft and coupling a movement of the at least one actuating element with a movement of the two branches;
wherein the number of grooves or undercuts of the two branches are sickle-shaped and have different radii.

2. The surgical electrode application instrument according to claim 1, wherein the actuating element is a manually actuatable pivot lever which is hinged to an instrument handle and which is provided and configured to manually apply the actuating force in an opening as well as in a closing direction.

3. The surgical electrode application instrument according to claim 2, wherein the instrument handle is arranged at the proximal end of the instrument shaft, and the gear or power transmission gear is partly arranged inside the instrument shaft.

4. The surgical electrode application instrument according to claim 1, wherein the two branches are identical in construction to each other and each have a branch neck which is axially offset in plan view and merges distally into the engagement portion arranged axially centrally in one piece.

5. The surgical electrode application instrument according to claim 4, wherein the branch neck is shaped like a platelet with a through bore at a distal transition portion between the branch neck and the engagement portion and an axially extending elongated hole in a proximal end portion of the branch neck, wherein the elongated hole is set at an angle to a longitudinal axis of a respective branch of the two branches.

6. The surgical electrode application instrument according to claim 5, wherein the branch neck is rotated by approximately 90° about a longitudinal branch axis with respect to the engagement portion in such a manner that the through bore and the elongated hole are oriented substantially along the number of grooves.

7. The surgical electrode application instrument according to claim 1, wherein the engagement portion is formed with a smooth surface on the radial outside of the engagement portion.

8. The surgical electrode application instrument of claim 1, wherein the grooves or undercuts run parallel in a transverse direction of each of the two opposite branches.

9. The surgical electrode application instrument of claim 1, wherein two grooves or undercuts of said number of grooves or undercuts have the same radius.

* * * * *